United States Patent [19]

Sauer et al.

[11] 4,024,166
[45] May 17, 1977

[54] PROCESS FOR THE PREPARATION OF 13β-ALKYL-4-GONENE-3,17-DIONES

[75] Inventors: Gerhard Sauer; Ulrich Eder; Gregor Haffer; Günter Neef; Rudolf Wiechert, all of Berlin, Germany

[73] Assignee: Schering Aktiengesellschaft, Berlin and Bergkamen, Germany

[22] Filed: Oct. 10, 1975

[21] Appl. No.: 621,384

[30] Foreign Application Priority Data

Oct. 11, 1974  Germany .......................... 2449031

[52] U.S. Cl. .......................... 260/397.3; 260/309.2; 260/340.7; 260/340.9; 260/397.4; 260/456 NS; 260/586 F
[51] Int. Cl.² .......................................... C07J 1/00
[58] Field of Search .................... 260/340.9, 397.3

[56] References Cited

UNITED STATES PATENTS 3,927,031  12/1975  Hajos .............................. 260/340.9
3,929,876  12/1975  Hajos .............................. 260/340.9

Primary Examiner—Ethel G. Love
Attorney, Agent, or Firm—Millen & White

[57] ABSTRACT

Novel process for the preparation of 13β-alkyl-4-gonene-3,17-diones of the formula

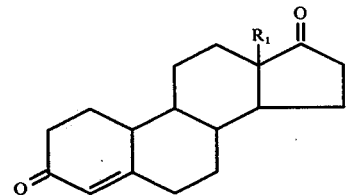

wherein $R_1$ is methyl or ethyl, consists of
reacting a 7aβ-alkyl,5,6,7,7a-tetrahydroindane-1,5-dione with formaldehyde and an arylsulfinic acid or an adduct of formaldehyde and arylsulfinic acid to produce a tetrahydroindane derivative;
hydrogenating the tetrahydroindane derivative with hydrogen in the presence of a palladium-, platinum-, or rhodium-containing hydrogenation catalyst to produce a perhydroindane derivative;
condensing the perhydroindane derivative in the presence of a proton-accepting agent with a 7,7-alkylenedioxy-3-oxooctanoic acid ester;
treating the product obtained with a strong aqueous base and then heating the product in an inert solvent to produce a 4,5-secosteroid;
hydrogenating the 4,5-secosteroid in the presence of a palladium-, platinum-, rhodium-, or nickel-containing hydrogenation catalyst; and
hydrolyzing and cyclizing the hydrogenated 4,5-secosteroid by treatment with a strong acid.

8 Claims, No Drawings

PROCESS FOR THE PREPARATION OF 13β-ALKYL-4-GONENE-3,17-DIONES

BACKGROUND OF THE INVENTION

This invention relates to a novel process for the preparation of 13β-alkyl-4-gonene-3,17-diones of the general Formula I

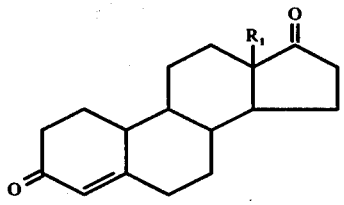

wherein $R_1$ is methyl or ethyl.

The 13β-alkyl-4-gonene-3,17-diones of general Formula I are known. These compounds are valuable intermediates for the preparation of pharmacologically effective steroids. They are utilized, for example, as starting materials for the synthesis of 17β-hydroxy-17α-ethynyl-13β-alkyl-4-gonen-3-ones and the corresponding esters which, are the active agents of oral contraceptives. See Annalen 702, 141 [1967], J. Chem. Soc. [1964], 4472.

Processes for the total synthetic production of 13β-alkyl-4-gonene-3,17-diones of general Formula I include those set forth in J. Org. Chem. 38, 3244 [1972] and J. Org. Chem. 37, 3385 [1972].

However, these conventional processes are very expensive, because numerous reaction steps are required for the total synthesis of these compounds, individual reaction steps can be conducted only at considerable technical expense, and the overall combined yields thus obtained are often unsatisfactorily low.

It is an object of this invention to provide a process for the total synthesis of 13β-alkyl-4-gonene-3,17-diones in a simpler manner than heretofore possible. It is a further object of this invention to provide a stereoselective synthesis of a perhydroindane intermediate having a trans-junction between the five- and six-membered rings by catalytic hydrogenation of a precursor 5,6,7,7a-tetrahydroindance compound. Other objects will become apparent to those skilled in the art.

SUMMARY OF THE INVENTION

According to the process of this invention, 13β-alkyl-4-gonene-3,17-diones (I) are prepared by:

a. reacting a 7aβ-alkyl-5,6,7,7a-tetrahydroindan-c-1,5-dione of the general Formula II

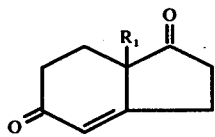

wherein $R_1$ is methyl or ethyl, with formaldehyde and an arylsulfinic acid of the general formula III

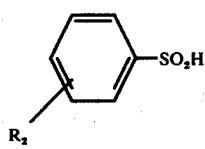

wherein $R_2$ is a hydrogen atom or lower alkyl of 1–4 carbon atoms which can be in the $o$-,$m$-, or $p$-position, or with the adduct of formaldehyde and the arylsulfinic acid, to produce a tetrahydronindane derivative of general Formula IV

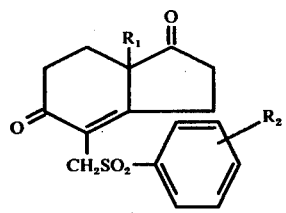

wherein $R_1$ and $R_2$ have the values given above, b. hydrogenating the tetrahydroindane derivative with hydrogen in the presence of a palladium-, platinum-, or rhodium-containing hydrogenation catalyst to produce a perhydroindane derivative of the general Formula V

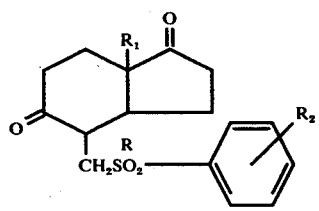

wherein $R_1$ and $R_2$ have the values given above.

c. condensing the perhydroindane derivative in the presence of a proton-accepting agent containing an alkali metal or alkaline earthmetal with an ester of the general Formula VI

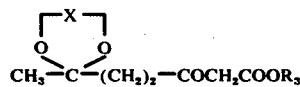

wherein X is an alkylidene of 2–6 carbon atoms or o-phenylene and $R_3$ is alkyl of 1–6 carbon atoms;

d. treating the obtained product thus with a strong aqueous base, and then heating the product in an inert solvent at about 60° to about 150° C. to produce a 4,5-secosteroid of the general Formula VII

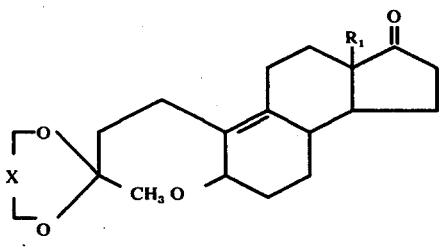

wherein X and $R_1$ have the values given above.

e. hydrogenating the 4,5-secosteroid with hydrogen in the presence of a palladium-, platinum-, rhodium-, or nickel-containing hydrogenation catalyst; and f. hydrolyzing and cyclizing the hydrogenated product by treatment with a strong acid.

DETAILED DISCUSSION

Suitable starting compounds for the process of this invention include the racemic 7aβ-alkyl-5,6,7,7a-tetrahydroindane-1,5-diones (J. Chem. Soc., London, 1959, 2022 and J. Org. Chem., 34, (1969) 107) as well as the optically active, readily available 7aβ-alkyl-5,6,7,7a-tetrahydroindane-1,5-diones (II), which can be produced by the method of German Unexamined Laid-Open Application DOS 2,014,757.

In the first reaction step, an indanedione (II) is reacted with formaldehyde and an arylsulfinic acid (III) or with the adduct of formaldehyde and the aryl sulfinic acid.

Arylsulfinic acids suitable for this reaction include those represented by the formula $R_2C_6H_4SO_2H$, wherein $R_2$ is $C_1$-$C_4$ alkyl or H— and $R_2$ is in the o-, m, or p-position with respect to the sulfinic acid group. Typical of these compounds are benzenesulfinic acid, the isomeric toluene-sulfinic acids, ethylbenzenesulfinic acid, and the like. For the practice of this invention, benzenesulfinic acid and p-toluenesulfinic acid are preferred because of their general availability.

Formaldehyde-arylsulfinic acid adducts suitable for use in this step include phenylhydroxymethylsulfone, p-tolylhydroxymethylsulfone or the like. The formaldehyde-arylsulfinic acid adducts are prepared by known methods (Chem. Berichte, 87, 1954, 135).

This first reaction step of the process of this invention can be carried out, for example, under the conditions described in DOS 2,221,704 whose disclosure is incorporated by reference. Preferably, this reaction step is effected using a mixture of 10–80% by volume of a tertiary amine and 20–90% of a lower carboxylic acid at a temperature from about 20° to about 80° C.

Typical tertiary amines which may be used include, for example, tertiary alkanolamines, such as triethanolamine, N,N-dimethylethanolamine, 2-pyrrolidinoethanol, and 2-morpholinoethanol; and tertiary diamines, such as tetramethylethylenediamine, tetramethylhexamethylenediamine, dimethylpiperazine and bis(dimethylamino)isopropanol.

Typical of suitable acids are, for example, formic acid, acetic acid, propionic acid, and butyric acid.

The tetrahydroindane derivative (IV) thus obtained is hydrogenated with hydrogen in a second reaction step, wherein the hydrogenation catalyst employed is a platinum-containing, rhodium-containing or palladium-containing catalyst. A catalyst containing palladium is preferred, especially a palladium-on-charcoal catalyst containing 2.5 – 30 % of palladium.

The hydrogenation step is conducted in a solvent, for example, a lower alcohol, a lower ketone, a lower carboxylic acid or mixtures thereof.

Lower alcohols, ketones, or acids of up to six carbon atoms are preferred. Examples of suitable alcohols, ketones, and carboxylic acids are: methanol, ethanol, propanol, isopropanol, butanol, sec.-butanol, tert.-butanol, amyl alcohol, or isoamyl alcohol, acetone, methyl ethyl ketone, diethyl ketone, methyl isobutyl ketone, formic acid, acetic acid, and propionic acid.

However, this hydrogenation step can also be conducted in other solvents or solvent mixtures. Exemplary of suitable solvent mixtures for the hydrogenation is a mixture of ethyl acetate and water.

To obtain a good yield of hydrogenation product, it is advantageous to add to the reaction mixture minor amounts of an acid, including mineral acids, sulfonic acids, and Lewis acids. Mineral acids include hydrochloric acid, sulfuric acid, phosphoric acid, and perchloric acid; sulfonic acids include p-toluenesulfonic acid; and Lewis acids include boron trifluoride, etherate, phosphorus oxychloride, phosphorus trichloride, manganese(II) chloride, and zinc(II) chloride. Preferably, 0.01–5.0% of one of the foregoing acids is added to the reaction mixture.

The hydrogenation is preferably conducted at a temperature from about 0° to about 80° C. and under a hydrogen pressure of 1 to 1000 atmospheres.

Although it is possible to hydrogenate compounds of Formula II under conditions other than those of the invention, other techniques result in incomplete hydrogenation or produce products lacking stereospecificity of the desired type or result in cleavage of the sulfonic acid group.

Thus, in another aspect, this invention relates to a method for the stereoselective synthesis of perhydroindane derivatives (V) having a trans-ring junction by hydrogenation of 5,6,7,7a-tetrahydroindane compounds (IV) with a hydrogenation catalyst selected from platinum-, rhodium-, and palladium-containing catalysts in a solvent selected from the group consisting of $C_1$–$C_6$ alcohols, ketones or carboxylic acids which contain minor amounts of a mineral acid, sulfonic acid or Lewis acid at a temperature from about 0° to about 80° C. and a hydrogen pressure from about 1 to about 1000 atmospheres.

The perhydroindane derivative (V) obtained is reacted in a third reaction step with a 7,7-alkylenedioxy-3oxo-octanoic acid ester (VI) in the presence of a proton-accepting agent which contains an alkali metal or an alkaline earth metal, the product obtained is treated with an aqueous, strong base, and then heated in an inert solvent from about 60° to about 150° C. to produce 4,5-seco steroids (VII).

In this reaction step, the arylsulfinyl group is eliminated. The resultant condensation product is cyclized, saponified, and decarboxylated by treatment with a base and subsequent thermal treatment.

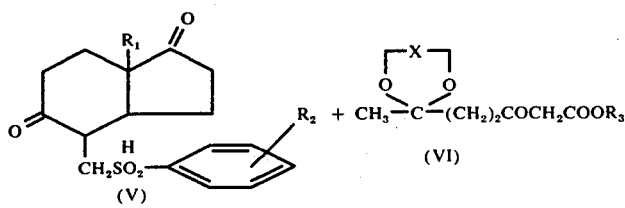

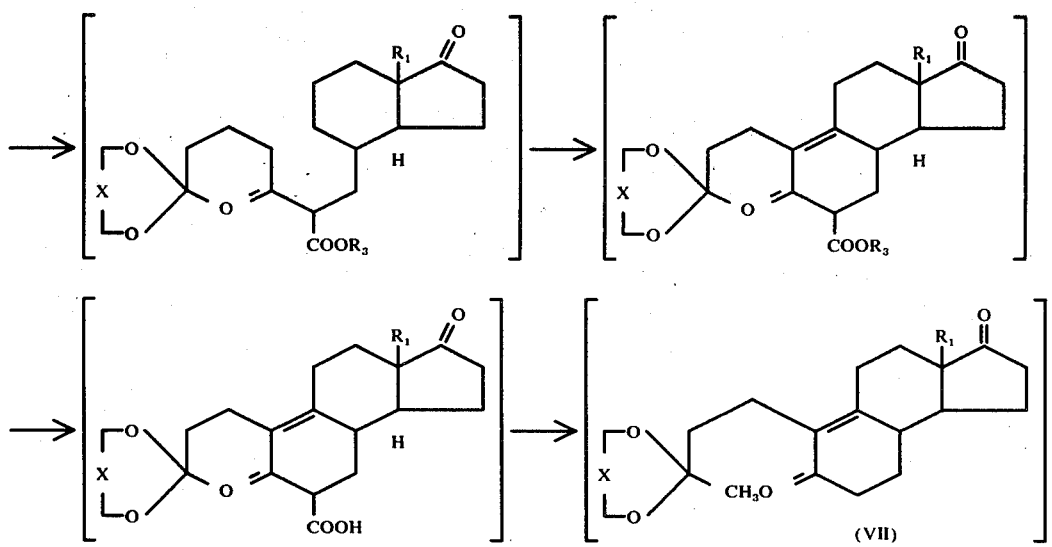

Esters (VI) for this reaction step include those in which X represents an ethylene group, a 1,3-propylene group, a 2,3-butylene group, a 2,2-dimethylpropylene group, or an o-phenylene group, and $R_3$ represents a methyl, ethyl, propyl, or butyl group.

Proton-accepting agents useful in this step of the reaction sequence include those which contain an alkali metal or alkaline earth metal, including alkali alcoholates e.g. sodium methylate, sodium ethylate or potassium tert-butylate or alkali amides, for example sodium amide.

Preferably, the proton-accepting agents utilized for this reaction step are alkali metal hydrides or alkaline earth metal hydrides, e.g. lithium hydride, sodium hydride, potassium hydride, or calcium hydride.

The condensation is preferably carried out in a nonpolar solvent. Nonpolar solvents usable for this reaction step include, for example, aliphatic, cycloaliphatic, or aromatic hydrocarbons of up to 12 carbon atoms dialkyl ethers of 4–12 carbon atoms. Examples of suitable hydrocarbons and ethers: pentane, hexane, octane, petroleum ether, cyclopentane, cyclohexane, benzene, toluene, xylene, diethyl ether, diisopropyl ether, and dibutyl ether.

The condensation is accomplished by first treating the ester of Formula VI with a proton-accepting agent and then reacting the resultant salt with the perhydroindane derivative of general Formula V.

Alternatively, this condensation step can be done by reacting the ester, the proton-acceptor and the perhydroindane derivative simultaneously in one of the aforementioned solvents.

This reaction step is preferably effected by using 1–5 moles of proton-accepting agent per mole of ester, at a reaction temperature of from about 0° to about 100° C.

Since the products are cyclized, saponified and/or decarboxylated to a certain extent while the reaction mixture is being worked up and since these reactions are part of the total synthesis, it is advantageous to work up the reaction mixture obtained during the condensation to crude product in the usual manner without observing any particular precautions and treat this crude product with a strong base in order to complete the cyclization and saponification of the ester. Suitable bases include, for example, alkali carbonates or alkali hydroxides, such as sodium carbonate, potassium carbonate, sodium hydroxide, or potassium hydroxide.

This treatment with a base is preferably done in the presence of water under the conditions usually used for saponification of esters. Suitable conditions include, for example, treatment of the products with aqueous solutions of strong bases in the presence of water-soluble alcohols such as dioxane, tetrahydrofuran, or glycol monomethyl ether; or of dipolar aprotic solvents including dimethylformamide, dimethyl sulfoxide, acetonitrile, and hexamethylphosphoric triamide. The reaction can also be done in a two-phase mixture containing in addition to the aqueous phase an inert water-insoluble solvent, such as chloroform, methylene chloride, tetrachloroethane, benzene, toluene, pentane, or cyclohexane.

The reaction mixture is worked up to the crude product in the usual manner, for example, by dissolution in an inert solvent and heating between about 50° and about 150° C. to complete the decarboxylation. Inert solvents suitable for this step include, for example, hydrocarbons, such as benzene, toluene, xylene, cyclohexane, pentane, hexane, decahydronaphthalene, and tetrahydronaphthalene; halogenated hydrocarbons, such as chlorobenzene, chloroform, dichloroethane, and tetrachloroethylene; and higher-boiling ethers, including as exemplary, glycol dimethyl ether, dioxane, tetrahydrofuran, di-n-butyl ether, diisopropyl ether, and anisole.

However, it is also possible to conduct this thermal treatment in the absence of solvents. Such a thermal decomposition offers no advantages, because it is more difficult to conduct commercially.

The 4,5-seco steroid of general Formula VII thus produced is hydrogenated in the presence of a catalyst which contains platinum, rhodium, nickel or palladium. A palladium-containing catalyst is preferred. Essentially, this reaction is done under the same conditions used for the hydrogenation of unsaturated ketones. Typically, the hydrogenation is effected using a solvent mixture consisting of a lower alcohol, e.g., methanol or ethanol, and a trialkyl amine, e.g., triethylamine or triisopropylamine.

After the hydrogenation has been completed, the catalyst, and optionally also the solvent, are removed in the usual manner and the resultant crude product is subjected to an acid treatment to split off the ketal group and to effect the subsequent cyclization. Suitable acids include, for example, aqueous mineral acids, such as hydrochloric acid, dilute sulfuric acid and dilute phosphoric acid. This acid treatment is conducted using the same solvents in connection with the treatment of the condensation products with strong bases.

In a preferred aspect of this invention:
the arylsulfinic acid is benzenesulfinic acid or p-toluene sulfinic acid;
the 5,6,7,7a-tetrahydroindane-1,5-dione is reacted with formaldehyde and said arylsulfinic acid in a mixture of 10–80% of a tertiary amine and 90–20% by volume of a lower carboxylic acid at a temperature from about 20° to about 80° C.;
the tetrahydroindane derivative is hydrogenated with a palladium-on-charcoal catalyst in an alcohol, ketone and/or acid containing up to six carbon atoms in a reaction mixture which contains a mineral acid, sulfonic acid or Lewis acid, at a temperature from about 0° to about 80° C. under a hydrogen pressure from about 1 to about 1000 atmospheres; and
the proton-accepting agent for the condensation of the perhydoindane derivative with the 7,7-alkylenedioxy-3-oxooctanoate is an alkali metal hydride or alkaline earth metal hydride.

Further conversion of the 13$\beta$-alkyl-4-gonene-3,17-diones prepared in accordance with this invention into pharmacologically active steroids is conventional, such as by reaction with acetylene under the conditions described in the U.S. Pat. No. 3,759,961. The thus obtained 17$\beta$-hydroxy-17$\alpha$-ethinyl-4-estrene-3-one and 17$\beta$-hydroxy- 17$\alpha$-ethinyl-18-methyl-4-estrene-3-one are used in contraceptives.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celcius; unless otherwise indicated, all parts and percentages are by weight.

EXAMPLE 1

13-methyl-4-estrene-3,17-dione a. 8.91 g. of optically active 7a$\beta$-ethyl-5,6,7,7a-tetrahydroindane-1,5-dione ($[\alpha]_D = +260°$), 8.53 g. of benzenesulfinic acid, and 1.80 g. of paraformaldehyde are combined with 30 ml. of triethanolamine and 10 m. of glacial acetic acid and heated for 60 hours under a nitrogen atmosphere to 50° C. in a sealed flask. The reaction mixture is then diluted with chloroform, washed with sodium bicarbonate solution, dilute hydrochloric acid, and water; the chloroform phase is concentrated under vacuum; and the residue is recrystallized from tetrachloromethane to yield 15.0 g. of 7a$\beta$-ethyl-4-(phenylsulfonylmethyl)-5,6,7,7a-tetrahydroindane-1,5-dione, m.p. 124°–125° C.

$[\alpha]_D^{20} = +198°$ (chloroform; $c = 1\%$).

b. 1.0 g. of the sulfone is combined with 180 ml. of ethanol, 1.8 ml. of 1N hydrochloric acid, and 100 mg. of 10% palladium-charcoal catalyst. The reaction mixture is hydrogenated with vigorous shaking for 40 minutes at room temperature. The catalyst is then filtered off, the solution is concentrated under vacuum, and the residue is recrystallized from ethanoldiisopropyl ether to yield 750 mg. of 7a$\beta$-ethyl-4-(phenylsulfonylmethyl)-perhydroindane-1,5-dione, m.p. 160°–161° C.

$[\alpha]_D^{20} = +82°$ (chloroform; $c = 1\%$).

c. 330 mg. of the perhydroindane compound produced in (b) is dissolved in 5 ml. of absolute benzene. The resultant solution is added to a mixture of 100 mg. of 85% sodium hydride, 50 ml. of pentane, and 0.33 ml. of 7,7-ethylenedioxy-3-oxooctanoic acid ethyl ester. The mixture is heated for 30 minutes under reflux, cooled in an ice bath, acidified with glacial acetic acid, and diluted with water. Then, the mixture is extracted with ether; the ether phase is washed and concentrated under vacuum.

The residue is dissolved in 20 ml. of methanol, cooled to 0° C., and combined in an argon atmosphere with 4 ml. of 10% aqueous sodium hydroxide solution. The mixture is agitated for 30 minutes at about 5° C., neutralized with glacial acetic acid, extracted with ethyl acetate, and the ethyl acetate phase washed and concentrated under vacuum.

The residue is dissolved in 25 ml. of benzene, refluxed for one hour and concentrated under vacuum. The resultant, crude product is 470 mg. of 3,3-ethylenedioxy-18-methyl-4,5-seco-9-estrene-5,17-dione.

d. The crude product thus obtained is mixed with 10 ml. of ethanol, 2 ml. of triethylamine, and 40 mg. of 5% palladium-charcoal catalyst and hydrogenated for 20 hours at 25° C. The catalyst is then filtered off and the filtrate solution combined with 3.9 ml. of 5N hydrochloric acid and heated for 5 hours under reflux. The solution is then concentrated under vacuum; the residue is taken up in chloroform, the chloroform phase is washed and concentrated under vacuum; and the residue is recrystallized from ethyl acetate-diisopropyl ether to give 180 mg. of 13-methyl-4-estrene-3,17-dione, m.p. 174°–176° C.

$[\alpha]_D^{20} = +98°$ (chloroform; $c = 1\%$).

EXAMPLE 2

4-estrene-3,17-dione a. 8.21 g. of optically active 7a$\beta$-methyl-5,6,7,7a-tetrahydroindane-1,5-dione ($[\alpha]_D = +360°$) is combined with 8.53 g. of benzenesulfinic acid, 1.80 g. of paraformaldehyde, 30 ml. of triethanolamine, and 10 ml. of glacial acetic acid and heated in a sealed flask under nitrogen for 40 hours at 50° C. The mixture is then diluted with propanol and poured into ice-cold sodium chloride solution; the precipitate obtained is filtered off and recrystallized from ethyl acetate to produce 12.3 g. of 7a$\beta$-methyl-4-(phenylsulfonylmethyl)-5,6,7,7a-tetrahydroindane-1,5-dione, m.p. 140°–146° C.

$[\alpha]_D^{20} = +223°$ (chloroform; $c = 1\%$).

20 g. of 7a$\beta$-methyl-4-(phenylsulfonylmethyl)-5,6,7,7a-tetrahydroindane-1,5-dione is dissolved in 1.6 liters of ethanol and 16 ml. of 1N HCl; 6 g. of Pd/C (10%), is added thereto. Within 2 hours of hydrogenation atmospheric pressure hydrogen at a temperature of 25° C., 2200 ml. of hydrogen is absorbed; the mixture is then filtered off from the catalyst, evaporated to dryness, taken up in chloroform, and extracted twice with water. After drying over magnesium sulfate and evaporation, 22.5 g. of an oily, hydrogenated sulfone is obtained.

c. 12 g. of this crude product is dissolved in 200 ml. of absolute benzene and added to a mixture of 2.0 g. of sodium hydride (80%) and 10 ml. of the ethyl ester of 7,7-ethylenedioxy-3-oxooctanoic acid in 100 ml. of absolute pentane and 100 ml. of absolute benzene. The mixture is agitated for 1 hour at 60° C. The sodium sulfinate which precipitates is removed by filtration and the filtrate is acidified with acetic acid. The mixture is then combined with water, extracted twice with chloroform, and the organic phase is dried with magnesium sulfate and evaporated.

The residue is combined with an ice-cold solution of 8 g. NaOH in 40 ml. of water and 200 ml. of methanol and allowed to stand for 15 minutes at room temperature. Thereafter, the mixture is concentrated to about 50 ml., taken up in water, and acidified with acetic acid. The product is extracted with ethyl acetate, and the extract is dried with magnesium sulfate and evaporated.

This crude product is dissolved in 100 ml. of benzene and refluxed for 1 hour. The solvent is removed by evaporation, resulting in 11.65 g. of an oily crude product.

d. Without further purification, the crude product is dissolved in 150 ml. of ethanol, and then 2 g. of Pd/C (5%) is added thereto and the mixture hydrogenated atmospheric pressure of hydrogen pressure at a temperature of 25° C. After the absorption of the stoichiometric amount of hydrogen, the mixture is filtered off from the catalyst, 40 ml. of dilute hydrochloric acid (N) is added thereto, and the mixture is heated for 1.5 hours under reflux. The solution is neutralized to pH 5 with 4N NaOH, concentrated to about 50 ml., and extracted three or four times with benzene. The organic solutions are washed with saturated sodium chloride solution and with water. Drying over magnesium sulfate yields a crude product in an amount of 10.5 g. Recrystallization from ethyl acetate-diisopropyl ether results in 6.1 g. of 4-estrene-3,17-dione, m.p. 163°–169° C.

$[\alpha]_D = + 140°$ (1% in chloroform).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of 13$\beta$-alkyl-4-gonene-3,17-diones of the formula

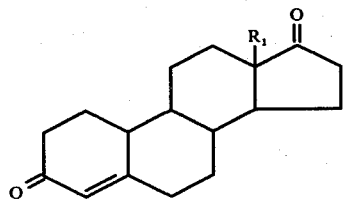

wherein $R_1$ is methyl or ethyl, which comprises:
a. reacting a 7a$\beta$-alkyl-5,6,7,7a-tetrahydroindane-1,5-dione of the formula

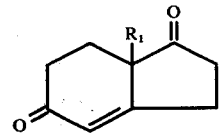

wherein $R_1$ is methyl or ethyl, with formaldehyde and an arylsulfinic acid of the formula

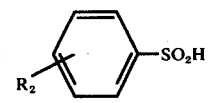

wherein $R_2$ is hydrogen or alkyl of 1–4 carbon atoms, or with an adduct of formaldehyde and the arylsulfinic acid, to produce a tetrahydroindane derivative of the formula

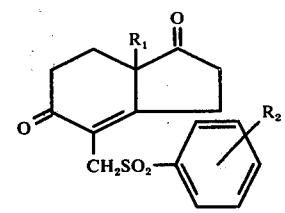

wherein $R_1$ and $R_2$ have the values given above;
b. hydrogenating the tetrahydroindane derivative with hydrogen in the presence of a palladium-, platinum-, or rhodium-containing hydrogenation catalyst to produce a perhydroindane derivative of the formula

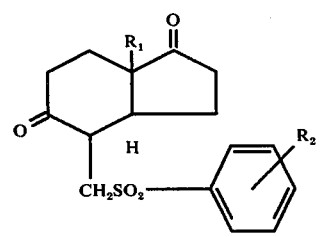

wherein $R_1$ and $R_2$ have the values given above;
c. condensing the perhydroindane derivative in the presence of a proton-accepting agent containing an alkali metal or alkaline earth metal with a 7,7-alkylenedioxy-3-oxooctanoate ester of the formula

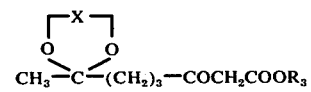

wherein X is an alkylidene of 2–6 carbon atoms or o-phenylene and $R_3$ is alkyl of 1–6 carbon atoms;
d. treating the product obtained with a strong aqueous base, and then heating the product in an inert solvent at about 60° to about 150° C. to produce a 4,5-secosteroid of the formula

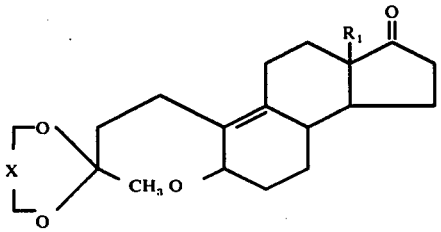

wherein X and $R_1$ have the values given above;
e. hydrogenating the 4,5-secosteroid with hydrogen in the presence of a palladium-, platinum-, rhodium-, or nickel-containing catalyst; and
f. hydrolyzing and cyclizing the hydrogenated 4,5-secosteroid by treatment with a strong acid.

2. The process of claim 1, wherein the arylsulfinic acid is benzenesulfinic acid or p-toluenesulfinic acid.

3. The process of claim 1, wherein the 5,6,7,7a-tetrahydroindane-1,5-dione is reacted with formaldehyde and the arylsulfinic acid in a mixture of 10–80% of a tertiary amine and 90–20% by volume of a lower carboxylic acid at a temperature from about 20° to about 80° C.

4. The process of claim 1, wherein the tetrahydroindane derivative is hydrogenated with a palladium-on-charcoal catalyst in a solvent selected from the group consisting of alcohols, ketones and carboxylic acids of up to six carbon atoms.

5. The process of claim 1, wherein the tetrahydroindane derivative is hydrogenated in a reaction mixture which contains a mineral acid, a sulfonic acid or a Lewis acid.

6. The process of claim 5, wherein the tetrahydroindane derivative is hydrogenated at a temperature from about 0° to about 80° C. under a hydrogen pressure from about 1 to about 1000 atmospheres.

7. The process of claim 1, wherein the proton-accepting agent for the condensation of the perhydroindane derivative with the 7,7-alkylenedioxy-3-oxooctanoate ester is an alkali metal hydride or an alkaline earth metal hydride.

8. The process of claim 1, wherein the arylsulfinic acid is benzenesulfinic acid or p-toluenesulfinic acid;
the 5,6,7,7a-tetrahydroindane-1,5-dione is reacted with formaldehyde and said arylsulfinic acid in a mixture of 10–80% of a tertiary amine and 90–20% by volume of a lower carboxylic acid at a temperature from about 20° C. to about 80° C.;
the tetrahydroindane derivative is hydrogenated with a palladium-on-charcoal catalyst in a solvent selected from the group consisting of alcohols, ketones and carboxylic acids of up to six carbon atoms in a reaction mixture which contains a mineral acid, sulfonic acid or a Lewis acid at a temperature from about 0° to about 80° C. under a hydrogen pressure from about 1 to about 1000 atmospheres; and
the proton-accepting agent for the condensation of the perhydroindane derivative with the 7,7-alkylenedioxy-3-oxooctanoate is an alkali metal hydride or alkaline earth metal hydride.

* * * * *